United States Patent
James et al.

(10) Patent No.: US 9,623,254 B2
(45) Date of Patent: Apr. 18, 2017

(54) FITTING AN AUDITORY PROSTHESIS

(71) Applicant: Cochlear Limited, Macquarie University (AU)

(72) Inventors: Christopher J. James, Toulouse (FR); Ibrahim Bouchataoui, Mechelen (BE); Mattheus J. P. Killian, Mechelen (BE); Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/854,785

(22) Filed: Sep. 15, 2015

(65) Prior Publication Data
US 2016/0045749 A1 Feb. 18, 2016

Related U.S. Application Data

(62) Division of application No. 12/914,206, filed on Oct. 28, 2010, now Pat. No. 9,155,886.

(51) Int. Cl.
- *A61N 1/372* (2006.01)
- *H04R 25/00* (2006.01)
- *A61N 1/36* (2006.01)

(52) U.S. Cl.
CPC ..... *A61N 1/37247* (2013.01); *A61N 1/36032* (2013.01); *H04R 25/606* (2013.01); (Continued)

(58) Field of Classification Search
CPC ............ A61N 1/37247; A61N 1/36032; H04R 25/70; A61B 5/12; A61B 5/121; (Continued)

(56) References Cited

U.S. PATENT DOCUMENTS 3,989,904 A 11/1976 Rohrer et al.
4,390,756 A * 6/1983 Hoffmann ............ G09B 21/009
607/56
(Continued)

FOREIGN PATENT DOCUMENTS

EP 2071873 A1 6/2009
JP 11-513539 11/1999
(Continued)

OTHER PUBLICATIONS

Patent Examination Report No. 1 for Australian Patent Application No. 2011322087 issued Jun. 30, 2014.
(Continued)

*Primary Examiner* — Adam J Eiseman
(74) *Attorney, Agent, or Firm* — Edell, Shapiro & Finnan, LLC

(57) ABSTRACT

A method and system for fitting and adjusting the operation of an acoustic hearing prosthesis or a hybrid electric and acoustic hearing prosthesis. A graphic user interface allows for the acoustic and electric fitting parameters to be viewed and adjusted in a comparable way. The method further allows for the parameters for acoustic stimulation of the acoustic channels to be adjusted in response to behavioral or objective measurement of response to known stimuli, so as to achieve a desired response curve.

20 Claims, 5 Drawing Sheets

(52) U.S. Cl.
CPC ......... *H04R 25/70* (2013.01); *H04R 2225/67* (2013.01); *H04R 2460/13* (2013.01)

(58) Field of Classification Search
CPC ......... A61B 5/123; A61B 5/125; A61B 5/126; A61B 5/6815–5/6817
See application file for complete search history.

(56) References Cited

U.S. PATENT DOCUMENTS

| | | | |
|---|---|---|---|
| 4,532,930 | A | 8/1985 | Crosby et al. |
| 5,724,433 | A | 3/1998 | Engebretson et al. |
| 5,758,651 | A | 6/1998 | Nygard et al. |
| 6,190,306 | B1 | 2/2001 | Kennedy |
| 6,205,360 | B1 | 3/2001 | Carter et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,697,674 | B2 | 2/2004 | Leysieffer |
| 6,915,166 | B1 | 7/2005 | Stecker et al. |
| 7,010,136 | B1 | 3/2006 | Roberts et al. |
| 7,076,308 | B1 | 7/2006 | Overstreet et al. |
| 7,117,038 | B1 | 10/2006 | Overstreet |
| 2002/0176584 | A1 | 11/2002 | Kates |
| 2004/0167586 | A1 | 8/2004 | Overstreet |
| 2005/0245991 | A1* | 11/2005 | Faltys .................... H04R 25/70 607/57 |
| 2006/0235332 | A1 | 10/2006 | Smoorenburg |
| 2006/0287690 | A1 | 12/2006 | Bouchataoui et al. |
| 2007/0255344 | A1 | 11/2007 | Van Dijk |
| 2010/0145411 | A1 | 6/2010 | Spitzer |
| 2011/0066210 | A1* | 3/2011 | Wilson ............... A61N 1/36032 607/57 |
| 2012/0109006 | A1 | 5/2012 | James et al. |

FOREIGN PATENT DOCUMENTS

| | | |
|---|---|---|
| WO | 2005122887 A1 | 12/2005 |
| WO | 2008031169 A1 | 3/2008 |

OTHER PUBLICATIONS

International Search Report and Written Opinion for PCT/AU2008/001865 mailed Mar. 12, 2009.
Japanese Office Action for Japanese Application No. 2010-538276 mailed Apr. 23, 2013 along with an English Translation.
International Search Report and Written Opinion for International Application No. PCT/IB2011/054808 mailed Apr. 27, 2012.
English translation of First Office Action in counterpart Chinese Application No. 201180052435.5, dated May 6, 2015, 10 pages.
Examination Report in corresponding European Application No. 11835727.6, dated Oct. 13, 2016, 3 pages.

* cited by examiner

AUDIOGRAM RIGHT

AUDIOGRAM LEFT

FITTING AN AUDITORY PROSTHESIS

CROSS-REFERENCE TO RELATED APPLICATION

The present application is a divisional application of co-pending U.S. patent application Ser. No. 12/914,206, filed on Oct. 28, 2010, the content of which is hereby incorporated by reference.

FIELD OF THE INVENTION

The present invention relates generally to auditory prostheses and more particularly to fitting an auditory prosthesis.

RELATED ART

Hearing aids are used to provide acoustic stimulation to assist hearing impaired persons. Cochlear implants have been used to assist those persons with more severe sensorineural hearing loss.

It has been recognized that there is a benefit for some users with hearing loss in providing both electrical stimulation and acoustic or mechanical stimulation, referred to hereafter as hybrid systems. Sensorineural hearing loss typically affects the higher frequency range most severely, corresponding to the more basal areas of the cochlea. As such, hybrid systems typically provide electrical stimulation in the higher frequency ranges, and mechanical stimulation in the lower frequency range.

The fitting and adjustment of such systems is conventionally carried out using two distinct fitting protocols. A first protocol is used for fitting the electrical part of stimulation, being similar to that used for a regular cochlear implant. Another protocol is used for the acoustic part of the stimulation, being comparable to that used for regular hearing aids.

These processes are conventionally carried out by a clinician making a lengthy series of psychophysical tests on separate acoustic and electric systems. This takes a considerable amount of time and effort, and appropriately trained personnel are a limited resource.

A further issue relates to young children. It can be difficult to reliably fit young children (or others) who are unable to communicate their percepts to the clinician.

It is disclosed in US Patent Application No. 2006/0287690 by Bouchataoui to use the acoustically evoked neural response, measured by the electrode components of the electrical stimulation system, to determine settings for acoustic signal processing. In particular, it is disclosed that these can be used to set the gain for each channel of the system, and to determine the cut off frequency between the acoustic and electrical stimulation modes.

SUMMARY

In a first aspect of the present invention, there is provided a method for adjusting the response curve of a hybrid hearing prosthesis system, the system including at least a filter bank, a processor, an. acoustic stimulator, an electrical stimulator and an electrode array, the filter bank. operatively providing output channel signals corresponding to amplitude in predefined channels, and the processor operatively applying input/output parameters to the output channel signals to produce acoustic stimuli, the method including: for each channel for which acoustic stimulation is contemplated, providing an acoustic stimulus at a known level; determining the evoked neural response to each stimulus using the. implanted electrode array; compiling the sum of evoked neural responses across multiple channels to produce a response curve, and comparing the response curve to a predetermined response curve; and adjusting one or more selected input/output parameters of one or more channels, so that the adjusted response curve best matches the predetermined response curve.

In a second aspect, there is provided a method for optimizing the response curve of a. hearing system including acoustic stimulation, the system including at least a filter bank, a processor, an acoustic stimulator, and at least one electrode, the filter bank operatively providing output channel signals corresponding to amplitude in predefined channels, and the processor operatively applying input/output parameters to the output channel signals to produce acoustic stimuli, the method comprising: for each acoustic channel, providing an acoustic stimulus at a known level; determining the evoked neural response to each stimulus using the implanted electrode; compiling the sum of evoked neural responses across multiple channels to produce a response curve, and comparing the response curve to a predetermined response curve; and adjusting one or more selected input/output parameters of one or more channels, so that the adjusted response curve best matches the predetermined response curve.

In a third aspect, there is provided a method for optimizing the response curve of a hearing system including acoustic stimulation, the system including at least a filter bank, a processor, and an acoustic or mechanical stimulator, the filter bank operatively providing channel signals corresponding to acoustic amplitude in predefined channels, and the processor operatively applying input/output parameters to the channel signals to produce acoustic stimuli within output channels, the method including: for each output channel, providing an acoustic stimulus at known level, so as to determine threshold and comfortable levels for the user; for each channel signal, varying the acoustic stimulus so as to determine desired aided output threshold, being a minimum acoustic level corresponding operatively to the threshold level for that channel; thereby defining the threshold, comfortable level and desired aided threshold for each channel for the user, and defining the fitting parameters by reference to those levels.

In a fourth aspect, there is provided a method of visualizing and controlling the stimulation parameters for a. hybrid device, the method comprising: displaying, by a graphic user interface (GUI), a set of electric channel indicators indicative of the threshold and comfort levels within each said channel; and displaying, by said GUI, a set of acoustic channel indicators indicative of the threshold and comfort levels within each said channel, said electric channel indicator and said acoustic channel indicators being scaled and displayed so as to be visible on a single display with visually comparable ranges.

In a fifth aspect, there is provided a method for fitting an acoustic device to a user, the device being a hearing prosthesis or the acoustic part of a hybrid device, the method comprising: for each channel, determining a minimum audible level desired for input sounds falling within the channel; determining the detection thresholds and comfort levels for acoustic stimulation by behavioral or objective measurements, and thereby deriving the acoustic stimulation processing parameters required for the channel.

BRIEF DESCRIPTION OF THE DRAWINGS

Illustrative embodiments of the present invention will now be described with reference to the accompanying figures, in which.

DETAILED DESCRIPTION

Figure 1:
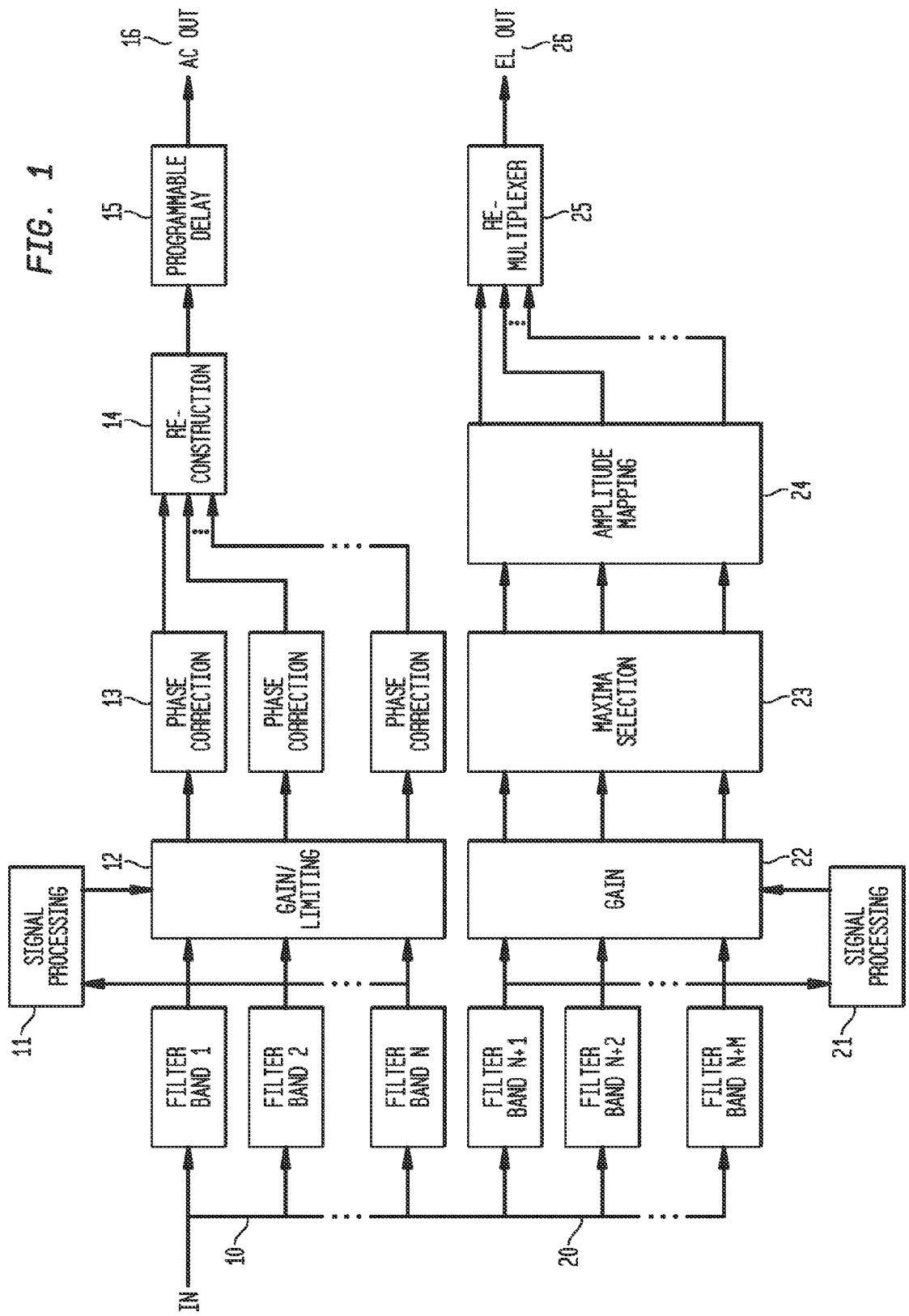
FIG. 1 is a schematic block diagram illustrating acoustic and electrical stimulation paths.

In a broad form, an embodiment of the present invention provides that in a system including acoustic or mechanical stimulation, such as a hybrid system, behavioural or objective responses to acoustic stimuli can be used to set the input output (I/O) functions for each acoustic channel, and the gains required to obtain the desired I/O functions adjusted for one or more channels, so that the actual response curve across channels matches a predetermined response curve.

In a further broad aspect, the embodiment provides a GUI based fitting method for hybrid systems, wherein the clinician can view the acoustic and electric channel settings on a single screen in a comparable way.

Embodiments of the present invention will be described with reference to a particular illustrative example, which is a fitting process for use in a hybrid electrical and acoustic or mechanical stimulation system. A hybrid system, for the purposes of the present specification and claims, is any auditory prosthesis which is. configured to apply more than one form of stimulation, such as electrical, acoustic, or mechanical stimulation. For example, in an embodiment, the hybrid system may apply both electrical and acoustic stimulation. The electrical stimulation may be, for example, applied via an intra-cochlea electrode array, or some other form of neural stimulation device. The acoustic stimulation may be any form of acoustic stimulation, such as, for example, stimulation applied using an external hearing aid (in the ear, in the canal, or otherwise) or earphone. The mechanical stimulation may include stimulation applied by, for example a. bone anchored hearing aid (BAHA) (also sometimes referred to as a bone conduction device), a middle ear or other implanted mechanical stimulator (e.g., an implanted mechanical actuator), or any other type of mechanical stimulation system.

As will be discussed further below, an embodiment of the present invention is applicable wherever a behavioral response or an evoked electrical response can be measured in a system using mechanical or acoustic stimulation, and it is not limited to hybrid devices. It is applicable to any form of acoustic or mechanical stimulation, such as those described above. It may be applied to a system with fully implanted components, a partly implanted system, or to a fully external system. The terms hybrid system or hybrid device should be construed in this broad way for the purposes of this patent application. The exemplary embodiment(s) also could be used in a solely acoustic or mechanical system, which may include a suitable implanted sensing electrode, or may include use of an observed behavioral response. It will be appreciated that the implementations are described for illustrative purposes, and their features are not intended to be limitative of the scope of the present invention.

A hybrid electric-acoustic hearing prosthesis, for the purposes of the present description of an exemplary embodiment, may comprise a cochlear implant that provides electrical stimulation, combined with an acoustic or mechanical stimulator, for example an ear-phone, a BABA or an implanted mechanical actuator. Electrical stimulation is commonly applied using electrical currents applied to a plurality of electrodes placed into the cochlea. Acoustic stimulation may be useful in cases where, for example, residual hearing function is still to be found in the low-frequency or apical region of the cochlea. In the present embodiment low-frequency sound may be provided through an acoustic or mechanical stimulation processing path (e.g., via a hearing aid, BABA or other mechanical device) and high frequency sounds may be provided through an electrical stimulation processing path (e.g., via infra-cochlea electrodes).

As noted, cochlear prostheses may apply electrical stimulation to a recipient's cochlea. This stimulation may be applied via direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear prosthetic device provides stimulation of the cochlear nucleus in the brainstem, such devices are often referred to as auditory brain stem implants (ABI).

Exemplary prostheses with which embodiments of the present invention may be implemented include, but are not limited to, those systems described in U.S. Pat. Nos. 4,532,930, 6,537,200, 6,565,503, 6,575,894 and 6,697,674, the entire contents and disclosures of which are hereby incorporated by reference herein. As described therein, cochlear prostheses generally include an external, wearable control unit that determines a pattern of electrical stimulation that is provided to an implanted stimulator unit containing active circuitry in a hermetic enclosure. Electrical stimuli are delivered through electrodes to provide electrical stimulation of auditory nerve cells.

FIG. 1 is an exemplary block diagram of a hybrid cochlear prosthesis configured to apply acoustic and electrical stimulation. As illustrated, the exemplary cochlear prosthesis comprises both acoustic and electric processing paths. It will be understood that this is only one of many such approaches for a hybrid cochlear prosthesis. The functional blocks illustrated in FIG. 1 may be implemented in, for example, the sound processor/receiver of the cochlear prosthesis. In this example, the sound processor/receiver may be referred to as a sound processor when used for applying electrical stimulation and a receiver when used for applying acoustic stimulation. These functional blocks may be implemented for example by hardware and/or software or a combination of same.

As illustrated, an input sound signal is received and presented to a filter bank, comprising a plurality of band-pass filters for filter bands 1 to N, labelled as 10, and a plurality of band-pass filter for filter bands N+1 to N+M, labelled as 20. As illustrated, the filter bands. 10 from 1 to N are processed within the acoustic processing path of the cochlear prosthesis, and filter bands 20 from N+1 to N+M are processed within the electrical path of the cochlear prosthesis. It will be appreciated that the frequencies processed along the acoustic and electrical paths may overlap in. some implementations. The values of N and M may depend upon the characteristics of the stimulation devices, the processing approach, and the stimulation strategy, as will be appreciated by those skilled in the art.

In the acoustic part, the outputs of band-pass filters 10 are provided to a. signal processor 11 for processing, and the gain/limiting controller 12. As will be described below, each of the signal processor 11 and gain limiting controller 12 process the signal according to the band levels and the input/output function. The signal for each channel is then provided to a phase corrector 13 for phase correction. A reconstructor 14 then combines the channels so as to construct an audio signal. The combined signal is then delayed by a programmable delay 15 and presented acoustically 16 to the recipient using, for example, a speaker. The delay helps improve synchronization between corresponding acoustic and electric stimuli. Generally electrical processing is more complex and may take a larger amount. of time to complete. As such, the programmable delay 15 may apply a delay to the acoustic signal from reconstructor 14 to synchronize the acoustic signal 16 and electric stimulation signal 26.

In the electrical processing path, the outputs of filters 20 are processed by a signal processor 21. A gain controller 22 applies a gain to the processed signal in accordance with predetermined parameters, determined as part of the fitting process. A maxima selector 23 may then select channels for application of stimulation in accordance with the speech processing strategy in use. Although in this example, a maxima selector 23 selects suitable maxima 23 bands 20 according to the determined speech processing strategy, in other embodiments different mechanisms may be used for selecting the channels for application of stimulation. The selected channels, including their amplitude, are then mapped by amplitude mapper 24 to corresponding electrodes (e.g., electrode 1, 2, . . . N) and current levels. The stimulation signals are then passed through the RF multiplexer 25 and output as stimulation instructions 26 for particular electrodes. This signal may then, for example, be transmitted to an internal component of the cochlear prosthesis where the instructions are processed by a stimulation controller that then provides stimulation via the electrodes in accordance with the instructions.

In such a system there are many individualized parameters to be determined in order to provide sound sensations which are sufficiently audible across a range of frequencies whilst maintaining comfortable and safe levels of stimulation. The specific parameters required for cochlear implant sound processing may vary somewhat between manufacturers and models. Commonly, it is required that the input sound dynamic range is "mapped" to the hearing range for each electrode or channel, defined by the minimum detectable electrical stimulation level, or threshold TE, and the maximum tolerable electrical stimulation level, or comfort level CE, for each intra-cochlear electrode.

In the case of electrical stimulation via cochlear implants, a nominal input dynamic range is commonly defined by the minimum input sound level $T_{SPL}$ that will produce electrical stimulation corresponding to $T_E$, and a sound level $C_{SPL}$ which will produce electrical stimulation at the comfort level $C_E$ for any given frequency analysis band. Some existing systems relate a particular electrode to a particular frequency channel, and it is this type of system that will be referred to specifically in the following example. However, some systems have virtual electrodes between the actual electrodes, in which a portion of the stimulation current is passed through neighboring electrodes, and the present invention is also applicable to such systems. In all these systems, there exists a transformation of input sound level, conveniently in decibels, to an electric output level expressed commonly as current amplitude in Amperes.

In the case of acoustic stimulation via an acoustic amplification prosthesis, usually in the form of an external hearing aid, the transformation remains in the acoustic domain with sound input transformed to sound output levels expressed in decibels sound pressure level (or Newtons for mechanical actuators).

In both cases the form of the input-output function may be linear or non-linear, the latter being commonly the case in cochlear implants. In addition, the function may be defined from a number of points (knee-points) joined by straight lines, as is commonly the case in acoustic prostheses. Between knee-points the functions may also be curved, typically according to logarithmic or exponential mathematical expressions, known as loudness growth functions.

Figure 2:
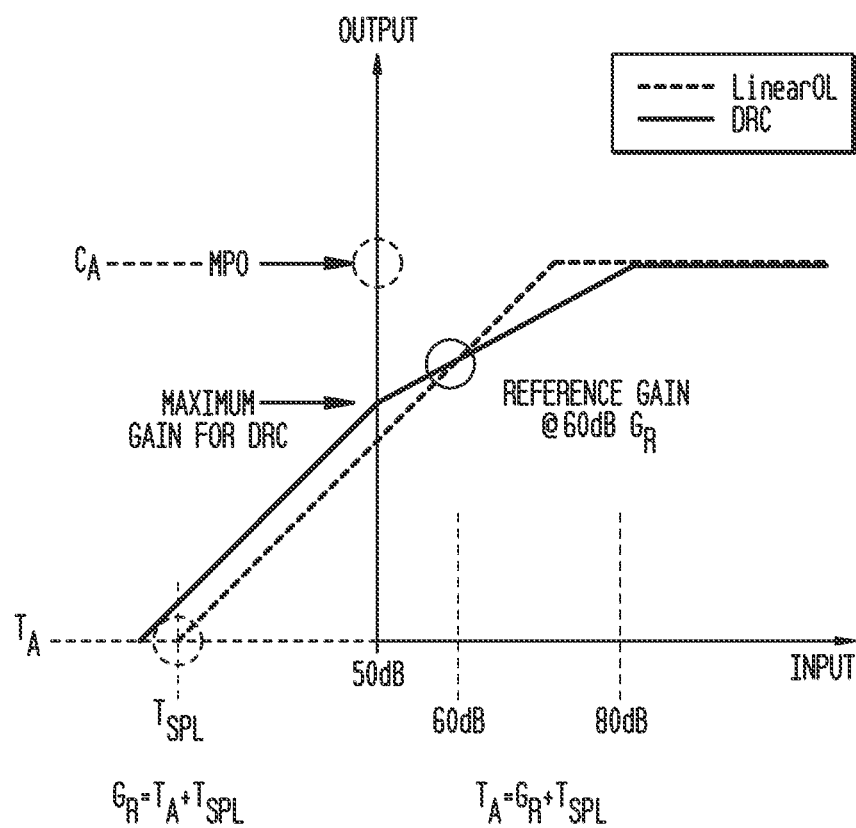
FIG. 2 is a graph illustrating the input output function for an acoustic channel.

Two types of common input-output function for acoustic stimulation are shown in FIG. 2: a so-called "Linear" gain function with additional output limiting (LinearOL dashed line), and a dynamic range compression function (DRC, sometimes called WDRC, solid line).

The LinearOL curve is simply defined by two parameters G and MPO: The difference between input and output levels, or the gain G, on the 1:1 sloping part of the function (or the intercept of the function. with the abscissa Input Level=0 dB) and the Maximum Output Power (MPO). The DRC curve is defined by two points, or two pairs of parameters: the maximum gain $G_{max}$ at a pre-defined input level (or lower knee-point), usually 40-50 dB, and the MPO at a second pre-defined input level (or upper knee-point), usually 80-90 dB. There may be additional parameters, for example the slope of the function below the lower knee-point may be greater than one, indicating an "expansion" region which acts to reduce the audibility of background noise. FIG. 2 accordingly illustrates the input/output function for each acoustic channel. The action of fitting parameters $T_A/G_R$, and $C_A/MPO$ are indicated by the circles.

Figure 3A:
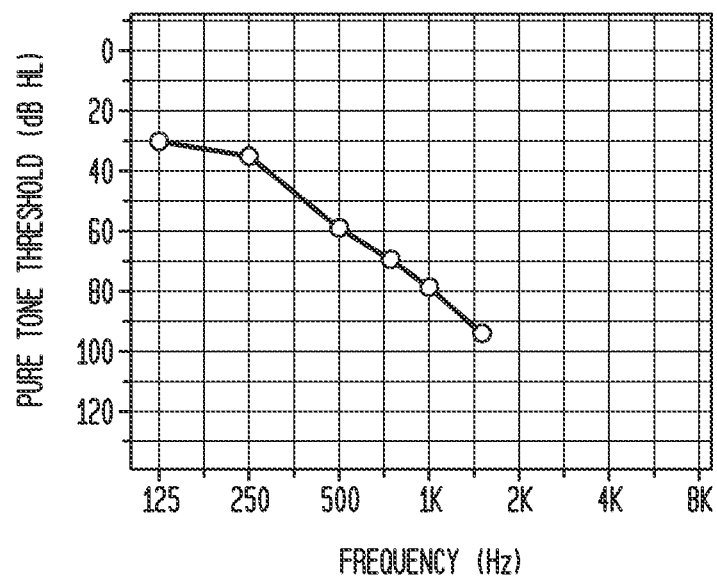
FIG. 3A is a graph illustrating a right side audiogram.
Figure 3B:
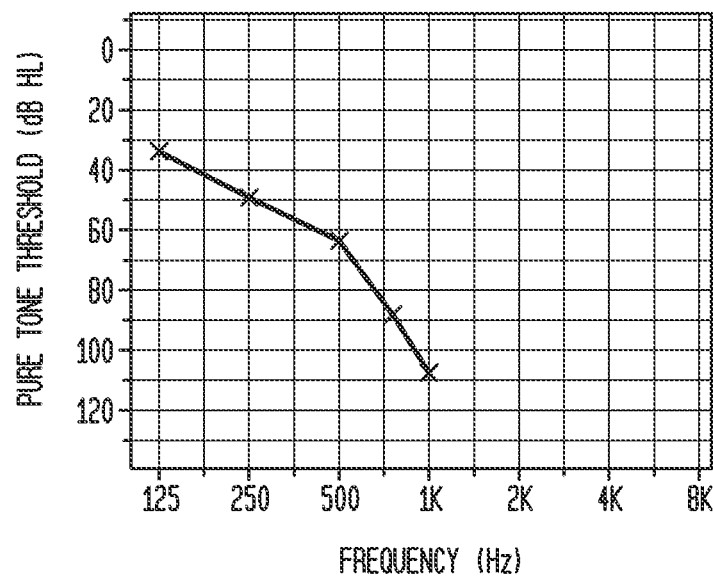
FIG. 3B is a graph illustrating a left side audiogram.

In acoustic hearing aids, the nominal gain G for each acoustic channel is derived from measurement of the individual's residual hearing function, along with the maximum power output MPO for that channel. The residual hearing sensitivity or "threshold" $T_{HL}$ and the maximum comfortable level (MCL or UCL) are commonly measured using a range of pure-tones of different frequency presented to each ear separately via standard audiological headphones. These measurements characterize each individual's residual hearing relative to "normal" listeners with average monaural thresholds of 0 dBHL. These data are commonly presented in a graph called an audiogram, such as illustrated in FIGS. 3A and 3B. FIGS. 3A and 3B show exemplary audiograms for right and left ears of a sample user, respectively.

Conventionally, the nominal gain and MPO for each audio channel are calculated from the value of THL using prescriptive rules. Various prescriptive formulae exist in the prior art based upon different rationales. These formulae incorporate the transformation of hearing characteristics in terms of dBHL to di3SPL, the difference between in-the-ear and external earphones, different vent sizes for ear-moulds, the characteristics of speech signals and the properties of impaired hearing, For example, the DSL rule has the rationale to restore the audibility of speech signals across a number of acoustic channels, whereas the NAL-RP rule incorporates the fact that a loss of high-frequency hearing, important for speech understanding, can be compensated for by providing additional audibility in the low frequencies. These prescriptive rules may be approximated by polynomial formulae of the form $a + b\, T_{HL} + c\, T^2_{HL}$ where the coefficients a, b and c are defined for each test frequency or acoustic channel with the corresponding $T_{HL}$ for that frequency.

Studies of individuals who have been implanted with cochlear implant electrodes and whose residual hearing function falls within the scope of the present embodiment indicate that such individuals generally prefer to use greater acoustic gain than is prescribed using prior art formulae, such as those described above.

Table 1 illustrates parameters in the prescription of optimal input/output characteristics of acoustic channels for a number of acoustic channel centre frequencies. In particular, it indicates the averages and ranges of the coefficients for each acoustic channel which best fit the preferred and optimal gains and MPOs.

Target gain $G = a_G + b_G \times T_{HL}$ and target $MPO = a_M + b_M \times T_{HL} + c_M \times T^2_{HL}$.

| f (Hz) | 110 | 300 | 460 | 560 | 700 | 830 | 1060 | 1570 |
|---|---|---|---|---|---|---|---|---|
| $a_G$ | −2.7806 | −1.4993 | −6 | −9 | −10 | −10 | −15 | −12 |
| $b_G$ | 0.5766 | 0.5475 | 0.57 | 0.6113 | 0.6342 | 0.65 | 0.6877 | 0.6877 |
| $a_M$ | 85.67 | 75.204 | 71 | 69.79 | 68.2 | 67.68 | 67.365 | 67.365 |
| $b_M$ | −0.2931 | 0.3704 | 0.422 | 0.4326 | 0.44 | 0.4337 | 0.425 | 0.425 |
| $c_M$ | 0.0088 | 0 | 0 | 0 | 0 | 0 | 0 | 0 |

The formulae are usually defined for each pure-tone test frequency to derive a gain G and MPO at each test frequency, and then where the test frequencies do not coincide with the centre frequencies of the acoustic channels the gain and MPO may be arrived at via interpolation. The nominal prescribed gain for each acoustic channel is most often defined for a 60 dB sound input, called $G_R$.

Using GR and MPO along with other fixed knee-point parameters for a given implementation, the complete input/output function for LinearOL or DRC schemes may be defined as in FIG. 2. The present use of GR as a reference is advantageous in that it allows for simple switching between schemes such as LinearOL and DRC according to user preference. Fine tuning of the frequency-gain and frequency-MPO response of the system can be achieved through simple controls, without resorting to direct manipulation of parameter variations such as compression ratio (the slope of the middle part of the gain function) and maximum gain, which might otherwise depend on the specific details of implementation.

In addition to the use of $G_R$ as a reference gain for each acoustic channel, the minimum audible level for sound heard through the sound processor $T_{SPL}$ may be defined as for a cochlear implant speech processor (FIG. 2). Detection thresholds $T_A$ and comfort levels $C_A$ may be measured for pure-tones corresponding to the centre frequencies of the acoustic channels. These signals may be generated through the sound processor/receiver thereby minimizing errors resulting from the averaging of receiver, ear canal and ear mould characteristics. This provides an alternative method to using $G_R$ and MPO to define the input/output functions of the acoustic channels. One particular advantage is that the minimum level for audibility of input sound signals is directly controlled via $T_{SPL}$. The input/output function can now be simply manipulated via $T_{SPL}$ using the measured parameters $T_A$ and $C_A$ in a similar way to typical cochlear implant sound processors. An additional advantage is that in the present implementation there are more acoustic channels for $T_A$ than there are standard test frequencies for $T_{HL}$ and accordingly the individual's residual hearing function may be better characterized and hence compensated for.

It will be appreciated that the use of $T_{SPL}$ is a new approach to fitting acoustic hearing prostheses, and allows for an improved mapping of channels and outputs levels to the user preferred thresholds.

Figure 4:
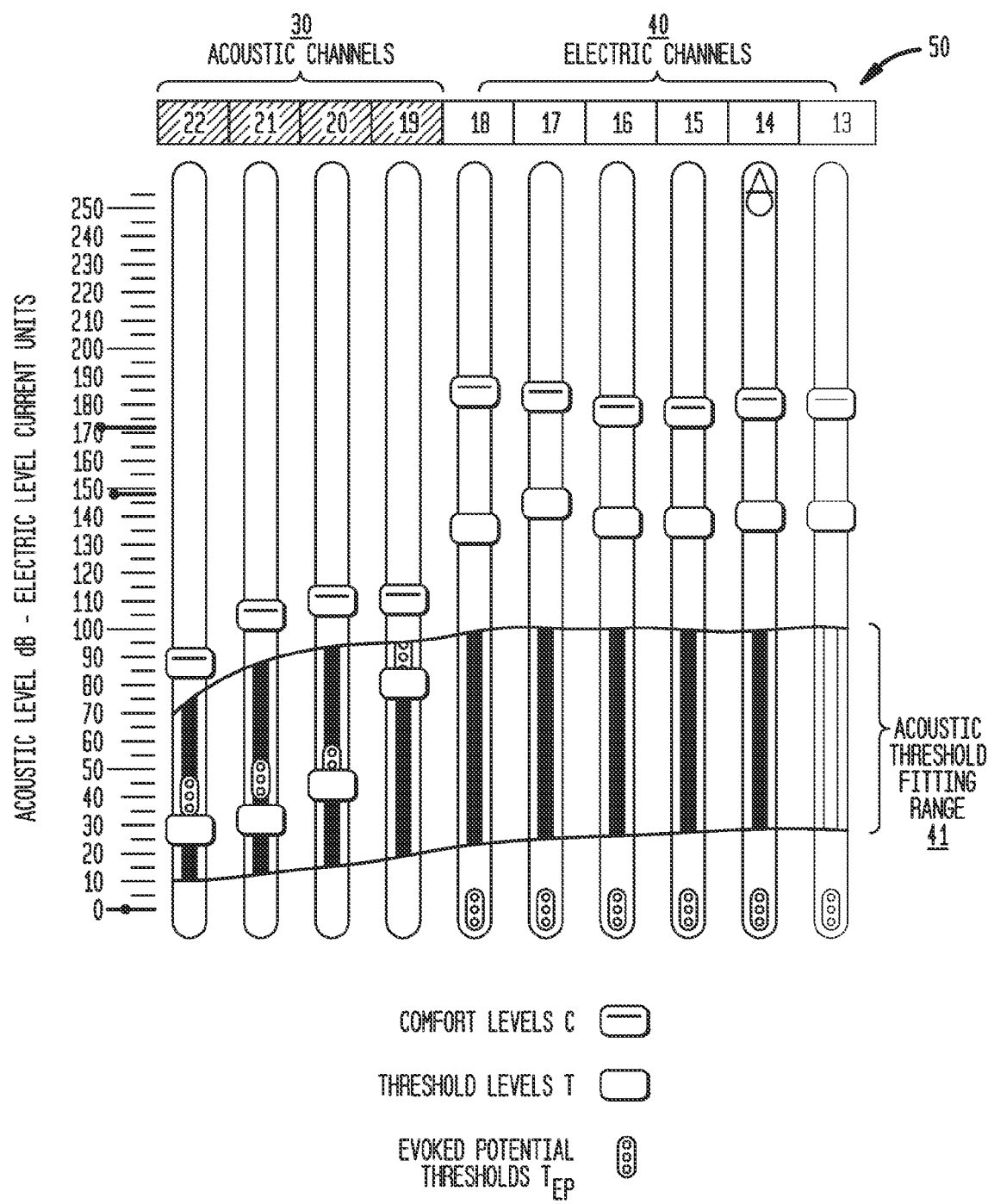
FIG. 4 is a conceptual screen shot of a. graphical user interface where the acoustic and electric channels are shown in a similar way.

A graphical user interface (GUI) is illustrated in FIG. 4 for the fitting of hybrid stimulation devices. This GUI may be displayed on any suitable display (e.g. . . . an LCD display) in accordance with instructions received from a computer or other suitable device executing the fitting method.

Acoustic channels 30 and electric channels 40 are presented to the user in a similar way: In the illustrated example thresholds $T_A$ and comfortable levels $C_A$ for acoustic stimulation for the left 4 channels, and thresholds $T_E$ and comfortable levels $C_E$ for electric stimulation for the remaining channels may be adjusted. In the illustrated GUI, a color may be associated with each input sound channel 50 to indicate whether it is being used for electrical or acoustic stimulation. A band 41 indicates graphically a suggested acoustic threshold fitting range.

There is no direct way to compare acoustic and electrical stimulation levels except, for example, by comparing threshold and comfortable loudness levels in individuals with residual hearing: However, in the example display the nominal acoustic sound-pressure levels will usually be less than 120 dB, indeed to be useful at all to the individual, and, using a suitable current level scale, the vast majority of individuals have minimum audible stimulation levels somewhat above 120 dB. Using such a display serves to provide data in an easily interpretable format for the fitting professional.

This latter described scheme employing $T_A$ and $C_A$ parameters measured through the acoustic signal path can be extended to acoustic or mechanical, external or implanted hearing prostheses which. stimulate across a wider range of frequencies and which do not incorporate an. electrical stimulation component (e.g. bone anchored hearing aids and middle-ear hearing prostheses).

This approach to an interface can also be employed where the channels for acoustic and electric stimulation overlap. In this case, a split vertical indicator could be used to show the electric and acoustic levels on the interface, or extra parallel channels provided. Thus, the entire fitting scheme for all forms of stimulation can be visualized at once by the fitting professional.

It will be understood that this interface allows for the levels to be not only viewed, but adjusted as required. For example, a mouse click on the appropriate bar allows (for example) the comfort level to be increased or decreased. The incorporation of this method of representation of residual hearing function is particularly desirable in a combined electric-acoustic fitting system and obviates the need for prescriptive rules for $G_R$ and MPO. However, it is also possible, through the use of a function such as in FIG. 2, to transform and therefore confirm the result of this kind of fitting method using the conventional representation of $G_R$ and MPO such as may be measured using a standard Real-Ear hearing-instrument test system.

The current embodiment is concerned with the optimum processing of low-frequency sound for individuals where high-frequency sensations are restored via electrical stimulation through a cochlear implant. Commonly in these individuals the slope of the residual hearing function is steep, and accordingly there can be large changes (e.g. >30 dB) in thresholds for adjacent test frequencies (half to one octave). It is therefore advantageous to have more acoustic channels than there are test frequencies in order to better approximate the desired, or "target", frequency-gain or frequency-MPO response obtained from the prescriptive rule.

Figure 5:
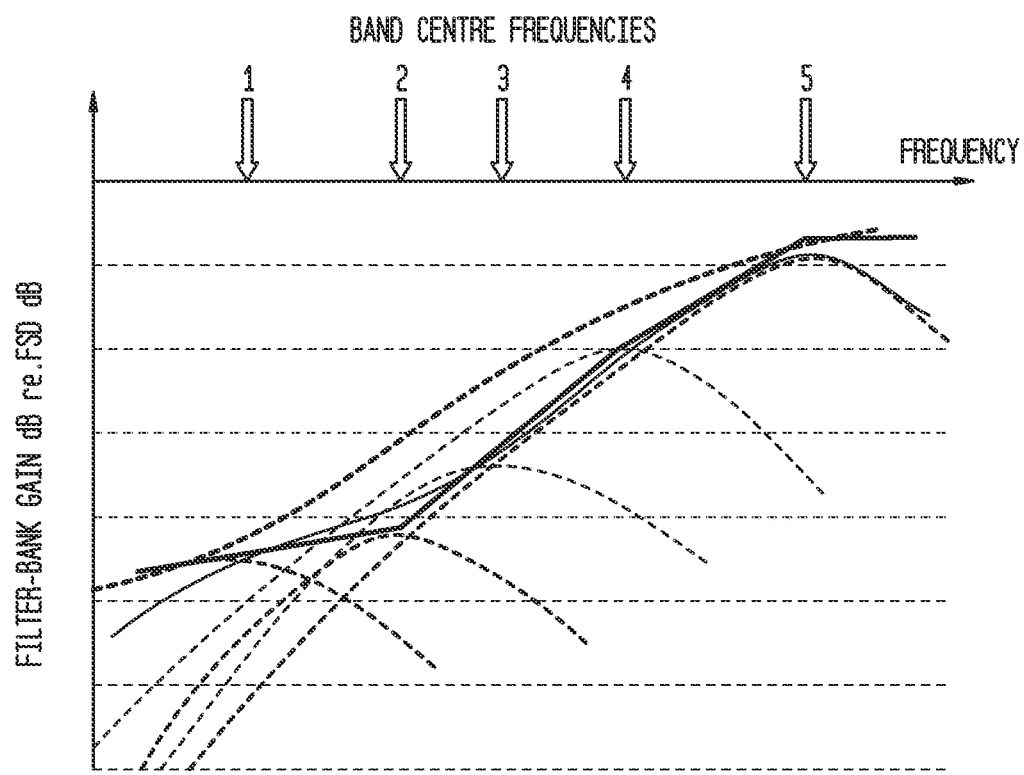
FIG. 5 is graph of gain at various frequencies, illustrating the process of matching to a desired response curve.

To further better match the actual frequency-gain response to the target response, in the present embodiment, there is the capability to adjust acoustic channels in order to avoid slope limitations imposed by the overlap of the underlying band-pass filters. The response for each individual acoustic channel to be set to the target maximum gain $G_{MAX}$ obtained either from a prescriptive rule and $T_{HL}$ as is known for prior systems or, is in the present embodiment of the invention, through the input/output function and the parameters $T_{SPL}$, $T_A$ and $C_A$. This is illustrated in FIG. 5.

Gains for the centre frequency of acoustic channels 1-5 are set to the target frequency-gain response (solid line). Due to the width of the underlying band-pass filters, the total frequency-gain response of the system (thick-dash line) does not correspond to that of the target. According to this embodiment of the present invention, by deactivating channels 3 and 4 the total frequency-gain response (thick-dotted line) better matches the target.

The total frequency-gain response of the combination of all acoustic channels is modeled and iterative adjustments are made to the response of each acoustic channel such that the best match is obtained between the desired target response and the actual response. Acoustic channels may be completely deactivated as in FIG. 5, or their response may be simply reduced so that when a dominant channel with a high gain (e.g. channel 4, FIG. 5) is in compression (i.e. when the instantaneous channel gain is less than $G_{MAX}$) sufficient gain is still provided in the lower frequency channels.

The use of a larger number of low-frequency channels also provides greater flexibility in the cross-over or cut-off frequency between acoustic channels and electric channels, which is required in order to optimally fit individuals with a wide range of residual hearing characteristics. This defines the frequency where stimulation changes from acoustic to electrical.

For frequencies above the cut-off, electrical stimulation is likely to produce more robust sensations. In addition, problems such as acoustic feedback (between the microphone of the sound processor and the output receiver of the acoustic path) are reduced when the bandwidth of the acoustic path is limited in order to avoid very high gains. In some cases the bandwidth of the electric processing path is not limited to frequencies above the cut-off, where the overlap of information provided by the acoustic and electric paths is advantageous to the individual.

In a hybrid stimulation device the upper limit in frequency for acoustic stimulation may be determined via a variety of means, for example:

At a frequency where thresholds $T_{HL}$ or $T_A$ for pure tones exceed a certain level, for example between 80-90 dB. This is illustrated in FIG. 4 where thresholds $T_A$ for channels 22-19 are within the acoustic threshold fitting range and those for channels 18 to 13 are above this range.

At a frequency where the amplification capacity of the acoustic channel is exceeded, for example for gains $G_R$ greater than 50-60 dB.

Where, due to loudness recruitment in the impaired ear, the difference between GR+60 and MPO, or TA and CA is less than 5-10 dB and would result in ineffective unmodulated output due to over compression.

At a frequency where there is no longer a neural response to acoustic stimulation.

As mentioned in the last case above, in the current embodiment, the cut off frequency may also be determined from measuring neural responses to acoustic or mechanical stimuli, such as the action potential generated by the cochlear nerve or the cochlear microphonic produced by remaining outer hair cells. These measures may be achieved using the integrated telemetry system, which includes the recording of neural responses via the cochlear implant electrodes and implant electronics.

Acoustically evoked potentials (EAPs) are neural responses which may be measured using tone pips to allow determination of residual hearing function for a range of low frequencies. The apical intracochlear electrodes are close to the region where residual hearing is expected and therefore the responses are expected to be relatively large as compared to when electrodes are placed on the promontory, outside the cochlea, as in classical electrocochleography.

For the intracochlear measurements according to the present implementation, the thresholds obtained for Acoustically Evoked Compound Action Potentials (CAP) are likely to be at or close to audiometric thresholds when recorded via a sensitive amplifier {noise level after averaging below 1 microvolt). This has already been. demonstrated for conventional electrocochleography (see for example Eggermont et al 1974). [Methods in electrocochleography. Acta Otolaryngol Suppl. 1974; 316:17-24.]

In the proposed setup acoustically evoked CAPs can be obtained by alternating the phase of short tone pips (10 ms) as in conventional electrocochleography. The tone pips should include short rise and fall times (to get rid of frequency splatter at the beginning and end of the stimulus). For the frequencies below 1 kHz one might choose longer tone pips to ensure that the tone pip contains at least several cycles. The tone pip can be applied through the acoustical part of a combined electric and acoustic stimulation system but one might also develop a device that puts the receiver far from the ear and delivers the acoustical stimulus through a tube if the receiver causes artifacts.

The recording of the electrophysiological signal is preferably implemented in a CI containing a battery or capacitor so that no RF has to be transmitted during the recording of the potential. Two buffers can be included in the sampling of the alternating stimuli. The individual buffers can be used to monitor the microphonics at a time period beyond the compound action potential. One could use longer stimuli to focus on recording of the microphonics. Based on the focus of the recording the filter settings of the amplifier can be adapted.

These latter methods would have the advantage that the cut-off frequency can be determined objectively such as is useful in the case of young children. In addition, the amplitude of the response or the threshold to obtain a response $T_{EP}$ can be used to determine values for $G_R$ or $T_A$ in a similar fashion to the determination of electric hearing thresholds from neural responses to electric stimulation. These values can be compared to the fitting range for acoustic thresholds (as illustrated in FIG. 4) in order to automatically select the cut-off frequency/acoustic-electric channel boundary.

The recordings can be used to give insight into the condition of hair cells, cochlear frequency selectivity and potentially neural disturbances such as neural synchrony and pathological adaptation. In these cases it may be better to reduce the cut-off frequency so that more of the complete frequency range is covered by electrical stimulation.

Evoked potentials may be recorded at the time of fitting of the device or recorded and stored automatically every time the sound processor is placed on the ear/head. In this way hearing can be monitored for changes on a daily basis and these changes are compensated for.

It will be appreciated that variations and additions are possible within the general scope of the invention described. All references cited are hereby incorporated by reference.

What is claimed is:

1. A method of visualizing and controlling stimulation parameters for a hybrid hearing prosthesis having both electric and acoustic channels for delivery of electric and acoustic stimulation, respectively, the method comprising:
displaying, at a display screen of a computing device, a graphical user interface (GUI) that includes a set of electric channel indicators indicative of threshold and comfort levels within each electric channel; and
displaying, within the GUI at the display screen, a set of acoustic channel indicators indicative of threshold and comfort levels within each acoustic channel,
wherein the set of electric channel indicators and the set of acoustic channel indicators are scaled and displayed so as to be visible simultaneously on the display screen within the GUI with visually comparable ranges, and wherein the GUI allows for the electric channel indicators and the acoustic channel indicators to be individually adjusted;
detecting adjustment of at least one of the electric channel indicators or the acoustic channel indicators; and
in response to the detected adjustment in of at least one of the electric channel indicators or the acoustic channel indicators, initiating an adjustment in a setting of the hybrid hearing prosthesis.

2. A method according to claim 1, wherein the channel indicators for the electric and acoustic channels include comfort and threshold icons that can be moved on the display interface.

3. A method according to claim 2, wherein at least some of the channels overlap in input acoustic range between acoustic channels and electric channels.

4. A method according to claim 2, wherein the GUI further permits one or more input acoustic ranges to be selected as any one of an acoustic channel, an electric channel, or both an acoustic channel and an electric channel, and to be changed between an acoustic channel and an electric channel.

5. A method according to claim 2, wherein values for evoked neural responses and/or behavioural responses to acoustic stimuli are recorded for at least selected acoustic and/or electric channels, and the values recorded for the evoked neural responses and/or the behavioral responses are used to automatically suggest values for threshold and comfort levels, and/or for selection of electric or acoustic stimulation.

6. A method according to claim 2, wherein detecting adjustment of at least one of the electric channel indicators or the acoustic channel indicator comprises:
detecting movement of at least one comfort or threshold icon associated with at least one electric or acoustic channel of the hybrid hearing prosthesis.

7. A method according to claim 6, further comprising:
in response to movement of the at least one comfort or threshold icon, initiating adjustment of at least one of comfort or threshold value at the at least one electric or acoustic channel of the hybrid hearing prosthesis.

8. A method according to claim 1, further comprising:
graphically displaying, within the GUI at the display screen, a suggested acoustic threshold fitting range.

9. A method performed at a processor coupled to an electric and acoustic hearing prosthesis and a display screen of a computing device, comprising:
determining acoustic threshold and comfort levels for a plurality of acoustic channels of the electric and acoustic hearing prosthesis;
determining electrical threshold and comfort levels for a plurality of electric channels of the electric and acoustic hearing prosthesis;
displaying, at the display screen, a set of acoustic channel icons representing the acoustic threshold and comfort levels within each of the plurality of acoustic channels; and
displaying, at the display screen, a set of electric channel icons representing the electrical threshold and comfort levels within each of the plurality of electric channels;
wherein the set of acoustic channel icons and the set of electric channel icons are scaled for simultaneous display within a graphical user interface on the display screen with visually comparable ranges, and wherein the graphical user interface is configured to allow for movement of the one or more of the electric channel icons or the acoustic channel icons on the display screen to adjust one or more of the electrical threshold and comfort levels or the acoustic threshold and comfort levels of the electric and acoustic hearing prosthesis.

10. The method of claim 9, further comprising:
detecting movement of at least one of the electric channel icons or the acoustic channel icons on the display screen; and
in response to the detected movement at least one of the electric channel icons or the acoustic channel icons, initiating an adjustment in a setting of the electric and acoustic hearing prosthesis.

11. The method of claim 10, wherein initiating an adjusting in a setting of the electric and acoustic hearing prosthesis comprises:
initiating adjustment of at least one of a comfort or threshold level at the at least one electric or acoustic channel of the electric and acoustic hearing prosthesis.

12. The method of claim 9, wherein an input acoustic range of at least one of the acoustic channels overlaps with an input acoustic range of at least one of the electric channels.

13. The method of claim 9, wherein the graphical user interface further permits one or more input acoustic ranges to be selected as any one of an acoustic channel, an electric channel, or both an acoustic channel and an electric channel, and to be changed between an acoustic channel and an electric channel.

14. The method of claim 9, wherein values for evoked neural responses and/or behavioral responses to acoustic stimuli are recorded for at least selected acoustic and/or electric channels, and the values recorded for the evoked neural responses and/or the behavioral responses are used to automatically suggest values for the threshold and comfort levels for an associated acoustic or electric channel, and/or for selection of electric or acoustic stimulation.

15. The method of claim 9, further comprising:
graphically displaying, within the graphical user interface at the display screen, a suggested acoustic threshold fitting range.

16. A computing device, comprising:
a display screen; and
one or more processors configured to:
  display, at the display screen, a set of acoustic channel icons representing acoustic threshold and comfort levels for each of a plurality of acoustic channels associated with an electric and acoustic hearing prosthesis;
  displaying, at the display screen, a set of electric channel icons representing electrical threshold and comfort levels for each of a plurality of electric channels associated with an electric and acoustic hearing prosthesis,
wherein the set of acoustic channel icons and the set of electric channel icons are scaled for simultaneous display within a graphical user interface on the display screen with visually comparable ranges;
detecting movement of at least one of the electric channel icons or the acoustic channel icons on the display screen; and
in response to the detected movement at least one of the electric channel icons or the acoustic channel icons, initiating an adjustment in a setting of the electric and acoustic hearing prosthesis.

17. The computing device of claim 16, wherein to initiate an adjusting in a setting of the electric and acoustic hearing prosthesis, the processor is configured to:
  initiate adjustment of at least one of a comfort or threshold level at the at least one electric or acoustic channel of the electric and acoustic hearing prosthesis.

18. The computing device of claim 16, wherein an input acoustic range of at least one of the acoustic channels overlaps with an input acoustic range of at least one of the electric channels.

19. The computing device of claim 16, wherein the GUI further permits one or more input acoustic ranges to be selected as any one of an acoustic channel, an electric channel, or both an acoustic channel and an electric channel, and to be changed between an acoustic channel and an electric channel.

20. The computing device of claim 16, wherein the processor is configured to:
  graphically display, within the GUI at the display screen, a suggested acoustic threshold fitting range.

* * * * *